United States Patent
Burdette et al.

(10) Patent No.: US 8,047,990 B2
(45) Date of Patent: Nov. 1, 2011

(54) COLLAGEN DENSITY AND STRUCTURAL CHANGE MEASUREMENT AND MAPPING IN TISSUE

(76) Inventors: Everette C. Burdette, Champaign, IL (US); Scott P. Huntley, Danville, CA (US)

(*) Notice: Subject to any disclaimer, the term of this patent is extended or adjusted under 35 U.S.C. 154(b) by 486 days.

(21) Appl. No.: 11/656,315

(22) Filed: Jan. 19, 2007

(65) Prior Publication Data

US 2007/0173720 A1    Jul. 26, 2007

Related U.S. Application Data

(60) Provisional application No. 60/760,220, filed on Jan. 19, 2006.

(51) Int. Cl.
*A61B 8/00* (2006.01)
(52) U.S. Cl. .................................. 600/438
(58) Field of Classification Search .......... 600/437
See application file for complete search history.

(56) References Cited

U.S. PATENT DOCUMENTS

| | | | |
|---|---|---|---|
| 6,067,371 A * | 5/2000 | Gouge et al. | 382/128 |
| 6,500,121 B1 | 12/2002 | Slayton et al. | |
| 7,229,411 B2 | 6/2007 | Slayton et al. | |
| 2005/0209588 A1 * | 9/2005 | Larson et al. | 606/27 |

* cited by examiner

*Primary Examiner* — Tse Chen
*Assistant Examiner* — Hien Nguyen
(74) *Attorney, Agent, or Firm* — Foley & Lardner LLP

(57) ABSTRACT

A method and system for two and three dimensional mapping of tissue density and/or structural changes from image data and/or spatial reflected or transmitted signal maps, and correlating the maps to changes in collagen density. The method and system includes the steps of: receiving an image or spatial maps of acoustic-derived RF signal data from tissue comprised of multiple pixels, segregating the image into groups of pixels, each group of pixels having characteristics within a defined class, establishing a baseline set of classes corresponding to initial conditions of the imaged/mapped tissue, measuring a differential in the set of classes for a group of pixels, the differential corresponding to a change in pixel values for the group of pixels, correlating said measured differential to a density change for the tissue corresponding to the group of pixels, and overlaying an indication of collagen density over the tissue image or mapped signal responses correlated with thermal dose indicating a change in collagen density for the tissue.

17 Claims, 9 Drawing Sheets

COLLAGEN DENSITY AND STRUCTURAL CHANGE MEASUREMENT AND MAPPING IN TISSUE

CROSS-REFERENCE TO RELATED PATENT APPLICATIONS

This application claims the benefit under 35 USC 119(e) of U.S. Provisional Application No. 60/760,220, filed Jan. 19, 2006, incorporated herein by reference in its entirety.

FIELD OF THE INVENTION

This invention relates to tissue monitoring and mapping equipment and methods, and more particularly, to methods and systems for monitoring and mapping changes in the collagen content and/or structures in tissue.

BACKGROUND OF INVENTION

Collagen is the major insoluble fibrous protein in the extra-cellular matrix and in connective tissue. There are at least nineteen types of collagen, but 80% to 90% of the collagen in the body is composed of the conventional well-known Type I, Type II, and Type III forms. The collagen molecule is a triple helix, each helical coil a biological polypeptide polymer constructed from glycine ($C_2H_5NO_2$), alanine ($C_3H_7NO_2$), proline ($C_5H_9NO_2$), and hydroproline ($C_5H_9NO_3$). As the three helices wrap around each other, hydrogen bonds form between each helix to maintain the structure. Collagen molecules pack together to form long, thin fibrils. The most prominent collagen types are:

Type I. The primary component of tendons, ligaments, and bones.
Type II. The primary protein constituent (more than 50%) in cartilage.
Type III. Strengthens the walls of hollow structures like arteries, the intestine, and the uterus.
Type IV. Forms the basal lamina (also called the basement membrane) of epithelia.

As a support structure, collagen fibrils are found in many environments within the body. The strength and relative elasticity of the collagen structure allow tendon and ligament structures to function in their role which requires great strength to manipulate skeletal structures. Up to 90% of the dry weight of tendons is collagen (at least 30% of the total weight), up to 50% of the dry weight of articular cartilage and synovial tissue is collagen (5% to 30% of total weight). Collagen comprises 75% of the dry weight of skin.

The helical structure and the nature of the hydrogen bond cross-linking of the collagen molecule cause it to react when heated. The cross-linking bonds break and the helix, which is a type of spring structure, collapses somewhat. The result is a shrinkage, not unlike the process which occurs when a woolen garment is washed in hot water and heated in a dryer. The amount of shrinkage is a function of time and temperature [see FIG. 1] and is well known.

Several therapeutic remedies have been developed which utilize the thermal response of collagen to affect shrinkage and/or for treating disease and, thereby, therapy. Among these are capsulorrhaphy, or the shrinkage of the tendon and capsular properties of the joints, shrinkage of the endopelvic fascia to address urinary incontinence, shrinkage of the bladder neck to affect treatment for urinary incontinence, shrinkage of sub-epidermal collagen for producing tightening of tissue to affect cosmetic outcomes, thermal treatment of benign and malignant tumors, among others.

A limitation of procedures for collagen shrinkage, however, is that the cell necrosis accompanying those procedures [see FIG. 1] weakens the structural integrity of the fibrils. It is known that shrinking capsular tissue more than 20% will weaken a structure so much that it will distort more under normal forces than it would if there had been no shrinkage at all [see FIG. 2]. Treatment of tumors usually involves delivering a thermal dose that guarantees cell necrosis, thus significantly changing collagen structure.

Thermally-induced shrinkage procedures have been received with moderate success because they have often produced variable results. Collagen shrinkage is a function of both time and temperature, but relatively small variations in either time or temperature can have dramatic results on the level of shrinkage [see FIG. 3]. Structures experiencing over-shrinkage are likely to have limited, or adverse results. Structures with insufficient shrinkage are likely to have limited results.

Some therapy systems measure tissue temperature during treatment using invasive probes and predict associated tissue modification, while others estimate the temperature based on power-time-temperature parametric curves established from imperical measurements. But, because thermal dose, and thus collagen shrinkage, is an integral function of both time and temperature in combination with spatial distribution, and since slight variations in temperature during a specific time period can cause dramatic changes in collagen shrinkage [see FIG. 3], temperature measurement alone is not truly sufficient. In response to the need to effectively determine dosage of the thermal treatment, a noninvasive measure of the thermal dose or its affects, including collagen changes, is badly needed.

Since optimizing collagen modification, including shrinkage, is the goal of specific procedures, what is needed is a system and method for directly measuring the shrinkage of the collagen structure, rather than temperature. A system and method which could monitor tissue properties concurrent with treatment, signaling the operator to halt thermal application when collagen shrinkage approaches 20% could produce greatly improved results [see FIG. 3], reducing the inconsistency associated with the thermal shrinkage procedures.

The limitations of the previous art for monitoring tissue treatment resulting from thermal injury are inadequate to provide information directly related to collagen changes sufficient to provide optimal control of extent of collagen structural modification, including shrinkage.

It has been demonstrated that changes in collagen content of tissue affects certain acoustic properties, namely the speed of sound in that tissue structure and the absorption of the acoustic energy as it passes through that tissue [see FIG. 4A]. It has been shown in the art that there is a linear function of both acoustic velocity and acoustic attenuation (see FIG. 4B) with variations in collagen content. Acoustic velocity changes 5 m/sec/(% change in collagen concentration) and acoustic attenuation changes 0.666 db/m/(% change in collagen concentration).

As an example, a 20% shrinkage in a collagen structure having an initial collagen content of 30% should cause a 25% increase in the % collagen by weight of the tissue structure. Since many collagen structures are 5% to 30% collagen (by weight), a 25% increase in density due to therapeutic shrinkage would cause a change in collagen content of 1.25% to 7.5%. These changes would correspond to changes in acoustic velocity of 6.25 m/sec to 37.5 m/sec, for initial collagen contents of 5% and 30%, respectively (see FIG. 5A). These changes would correspond to changes in acoustic attenuation of 0.833 db/m to 5 db/m, respectively [see FIG. 5B].

In addition to changes in acoustic velocity and attenuation, the structural patterns of the tissue change permanently as a function of thermally-induced necrosis and density changes. These patterns may be characterized in an analysis of the structures in the 2D or 3D acoustic image or in 2D spatial maps of acoustic signals that are reflected from or transmitted through the tissue in those locations. Applying pattern recognition methods and/or expert system techniques to the backscatter image or signal mapping data can yield useful information in addition to attenuation and velocity measurements alone.

Ultrasound (acoustic) imaging has been used in medical imaging for years to differentiate tissue structures. These imaging techniques have examined acoustic properties of ultrasound waves as they travel through and reflect off of tissue to distinguish tissue types and the boundaries between those types. These devices map tissue in two dimensions (along a plane in line with an imaging transducer) or three dimensions (by using multi-element imaging transducers or single-line imaging transducers whose focus or location changes during the process. Two of the acoustic properties used in these imaging techniques are acoustic velocity and acoustic attenuation. Further, structural change analyses using pattern recognition methods can provide an ability to track changes in tissue structure/collagen structure from baseline using backscattered image information.

The ability to map those changes in tissue and assign changes in collagen density to the mapped functions would allow users the ability to monitor, in real time, the therapy effect they are seeking to accomplish.

SUMMARY OF THE INVENTION

The subject invention therefore includes a system and method for mapping acoustic changes from an ultrasound image of tissue induced by a structural change or thermal injury and mapping that information in a pixilated form. That is, each pixel, or square, in a two dimensional image or each voxel, or cube, in a three dimensional image, will be assigned acoustic characteristics based on the backscattered signal from that region and/or based on the transmitted signal through a specific tissue region. In particular, such system and method shall assign acoustic velocity values and acoustic attenuation values to each of the pixels.

As the treatment proceeds, the system and method will assign change values, and assign changes in collagen content concentration to those change values, to the acoustic properties for each pixel. The changes preferably are color-coded to make interpretation of the changes easier for users who are not familiar with interpreting ultrasound images.

An object of the invention is to provide an improved system and method to assign patterns or classes to groups of pixels or voxels for specific collagen changes based upon the backscatter patterns in the ultrasound image. Specific types of changes in patterns are correlated with known classes of patterns for groups of pixels.

Another object of this invention is to provide an improved system and method to correlate changes in the acoustic properties directly to changes in the collagen content in tissue and use those changes in acoustic properties to provide feedback for the application of thermal energy during a collagen shrinkage procedure.

Another object of this invention is to provide an improved system and method to determine acoustic property changes characteristic of the spatial representations of an acoustic signal and using those assignments to create a two dimensional or three dimensional map of the changes in collagen concentration of a tissue structure.

Another object of this invention is to provide an improved system and method to use color-coding when displaying the two dimensional or three dimensional maps of changes in collagen density.

Another object of this invention is to provide an improved system and method to use color-coding when displaying the two dimensional or three dimensional maps of changes in structural patterns in groups of pixels/voxels which correspond to changes in collagen structure and/or content.

Another object of this invention is to provide an improved system and method to measure the structural patterns of the tissue that are affected as a function of thermally-induced necrosis and density changes. These patterns may be characterized in an analysis of the structures in the acoustic image or in 2D spatial maps of acoustic signals that are reflected from or transmitted through the tissue in those locations. Applying pattern recognition methods to the image or signal mapping data can yield useful information in addition to attenuation and velocity measurements alone.

Another object of this invention is to provide an improved system and method to cross-correlate each of the types of measured changes in pairs or in total with each other to provide a sensitive system and method for determining changes in tissue collagen, including shrinkage and tissue necrosis.

Another object of this invention is to provide an improved system and method to use the measured tissue changes to correlate to tissue damage with changes in tissue structure and/or acoustic property changes as a result of treatment.

Since essentially all human tissue contains collagen in the interstitial tissue and since this invention describes measurements of changes in collagen concentration and/or collagen structure, and since changes in collagen concentration and structure occur in most thermal treatments, particularly those treatments intended to shrink collagen structures, this invention is applicable for monitoring collagen shrinkage procedures in all tissue structures of all types, both external and internal.

Further advantages and features of the invention will be apparent from the following specifications, claims and drawings, illustrating the preferred embodiments of the invention.

DETAILED DESCRIPTION OF PREFERRED EMBODIMENTS

The subject invention includes a system and method for mapping acoustic changes from an ultrasound image of tissue induced by a structural change or controlled thermal injury and mapping that information in a pixilated form. That is, each pixel, or square, in a two dimensional image or each voxel, or cube, in a three dimensional image, will be assigned acoustic characteristics based on the backscattered signal from that region and/or based on the transmitted signal through a specific tissue region. In particular, such a system and method assigns acoustic velocity values and acoustic attenuation values to each of the pixels.

As the treatment proceeds, the system and method will assign change values, and assign changes in collagen content concentration to those change values, to the acoustic properties for each pixel. The changes are most preferably color-coded to make interpretation of the changes easier for users who are not familiar with interpreting ultrasound images.

Figure 1:
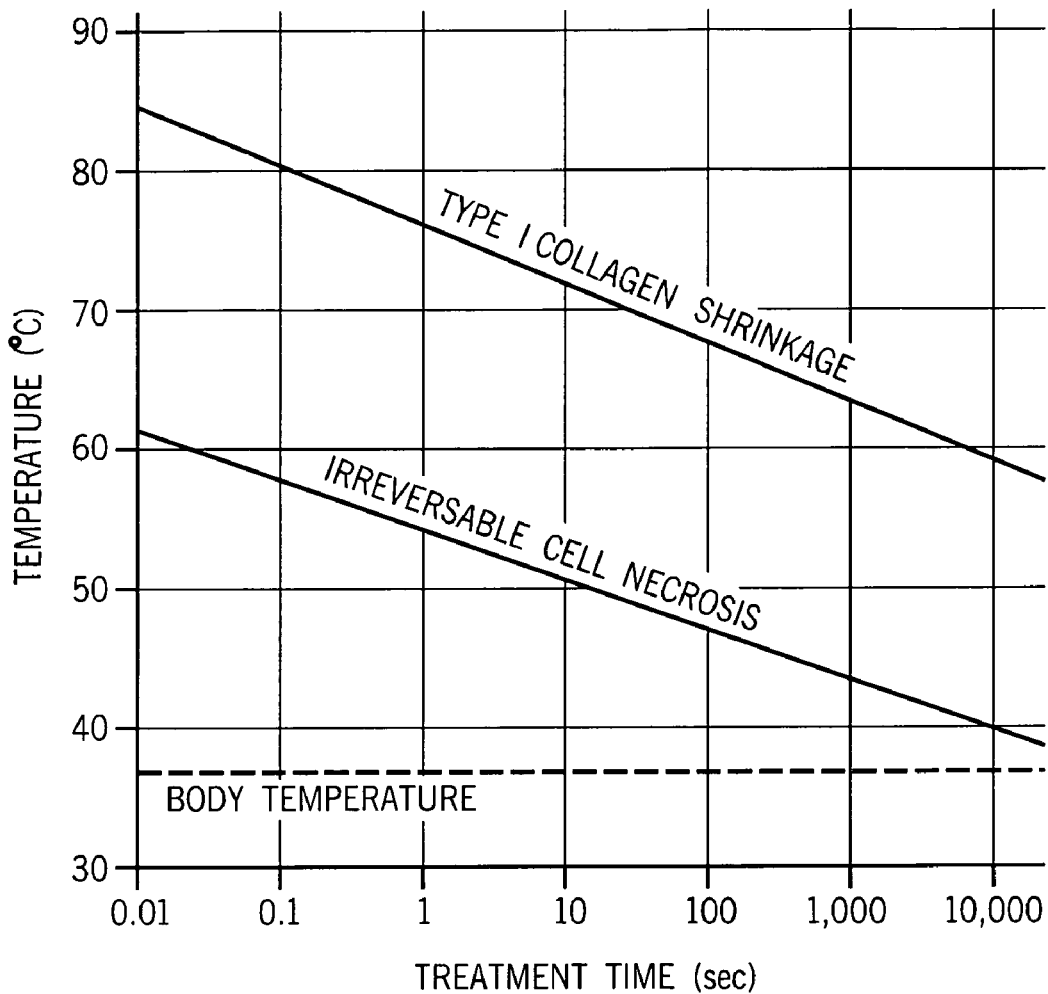
FIG. 1 shows thermal effects on tissue.
Figure 2:
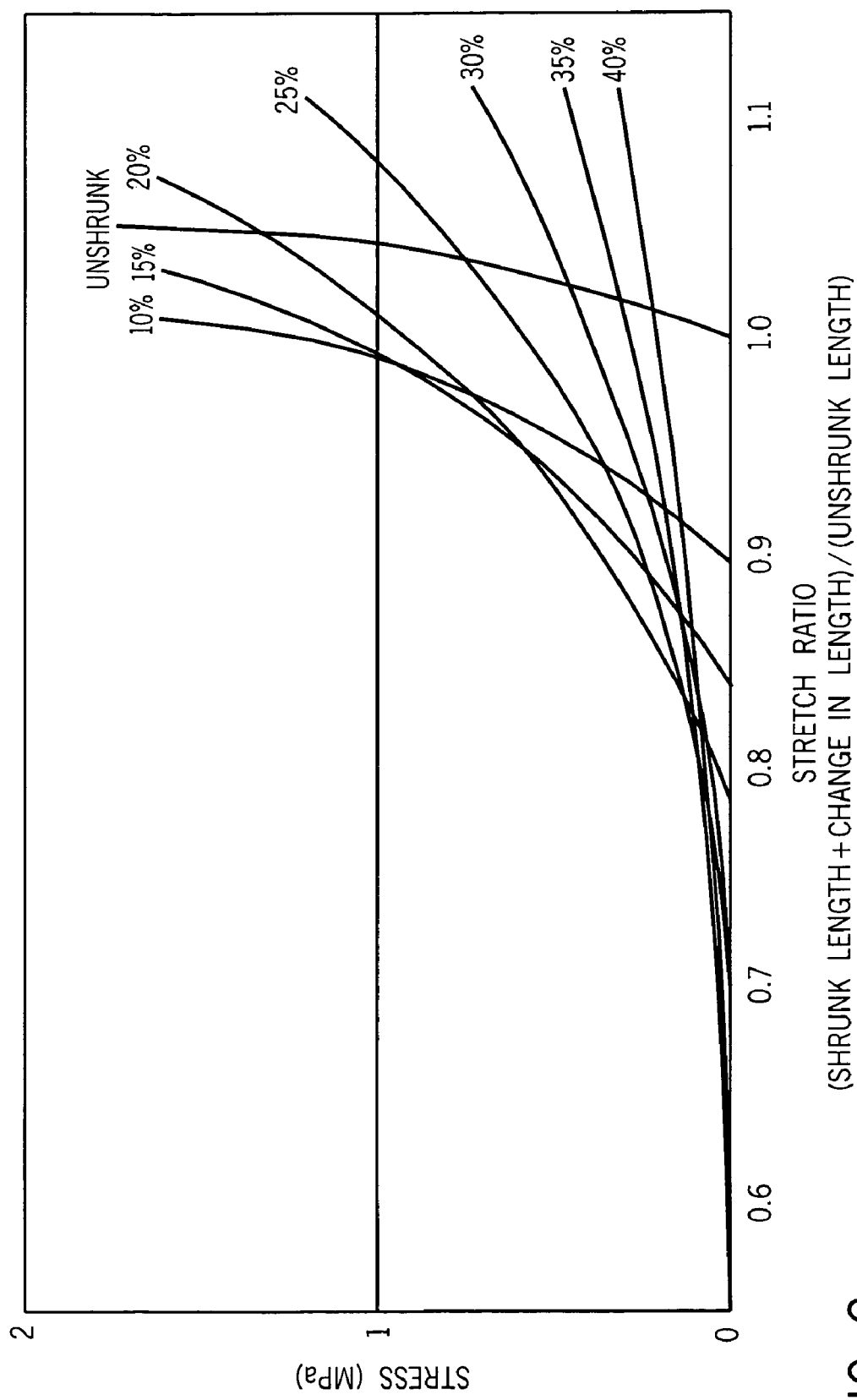
FIG. 2 shows strength of collagen containing tissue post thermal remodeling.
Figure 3:
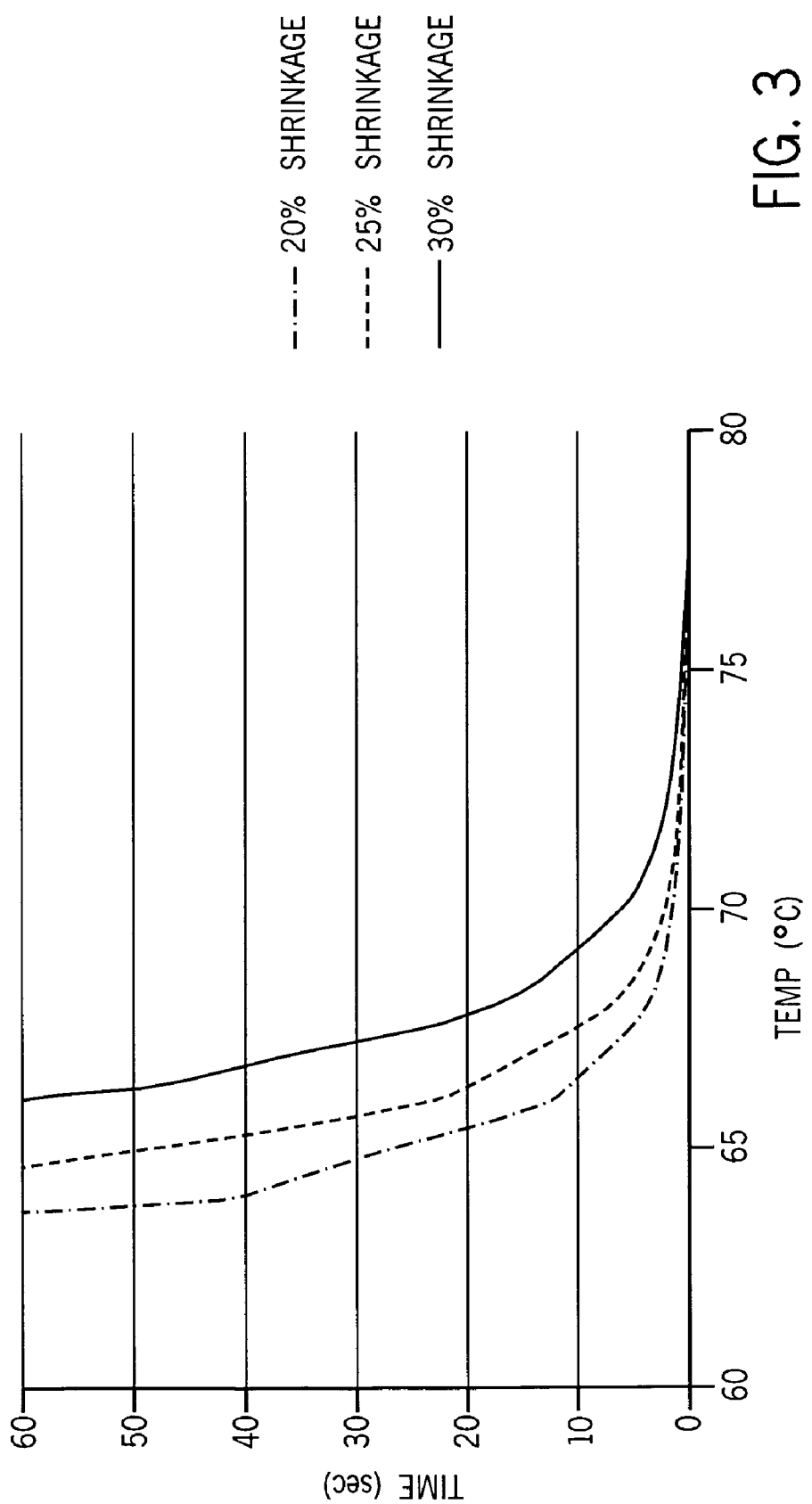
FIG. 3 shows time/temperature influences on collagen shrinkage.
Figure 4A:
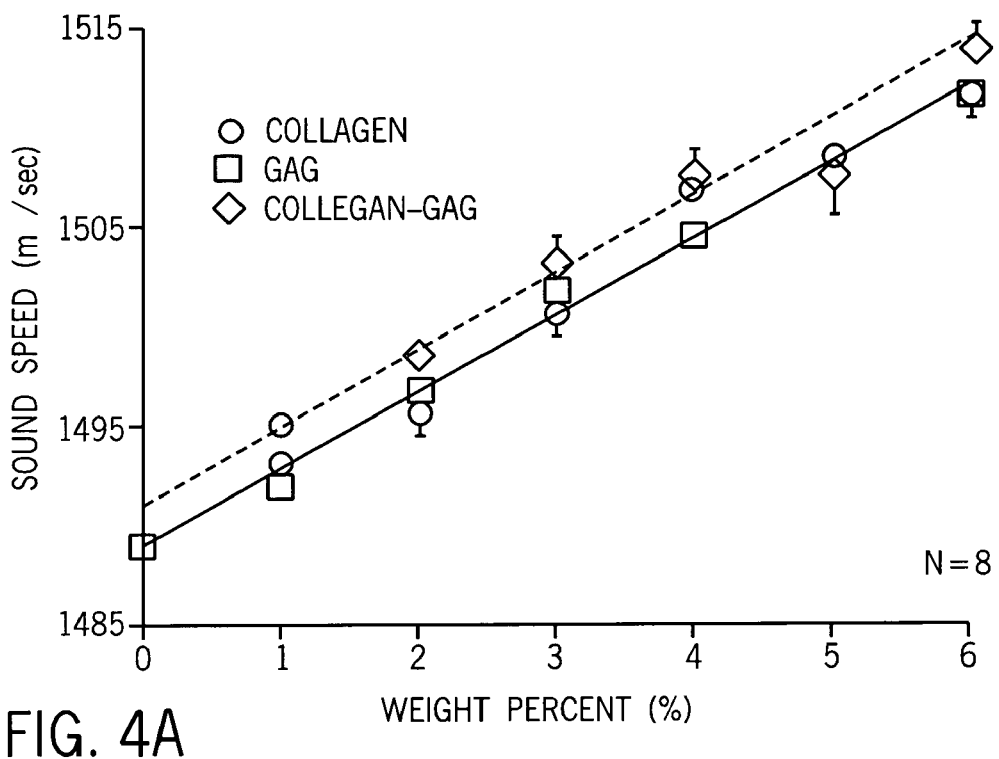
FIG. 4A shows relative changes in acoustic velocity and FIG. 4B acoustic attenuation properties with respect to changes in the collagen content of tissue.
Figure 4B:
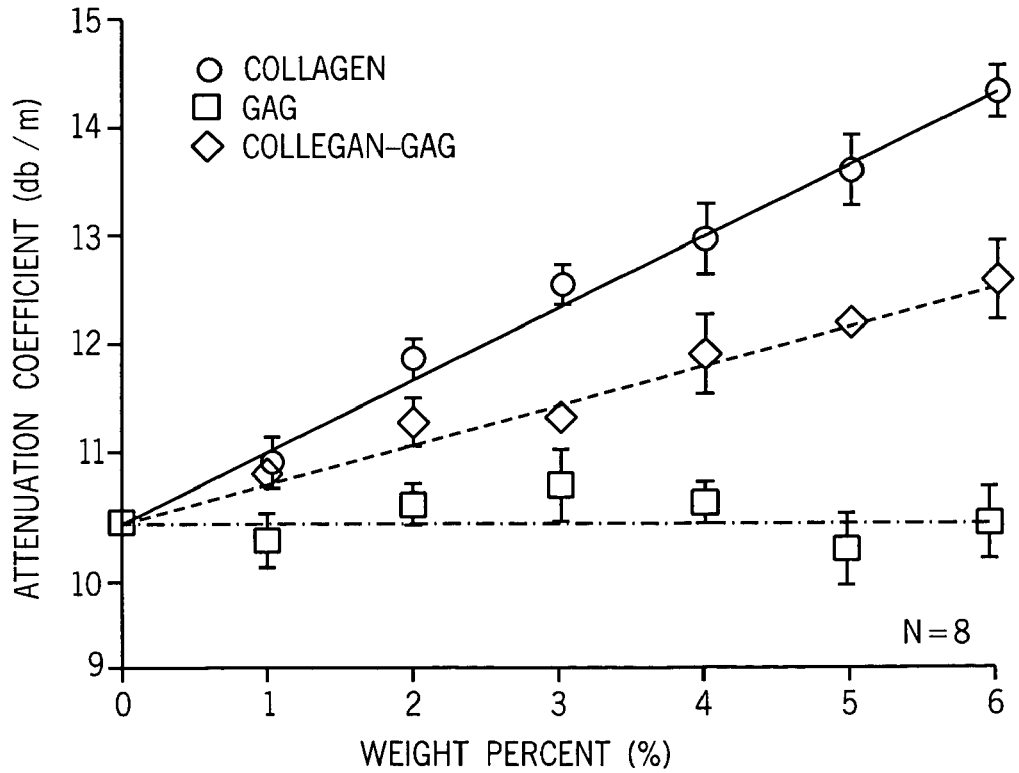
Figure 5A:
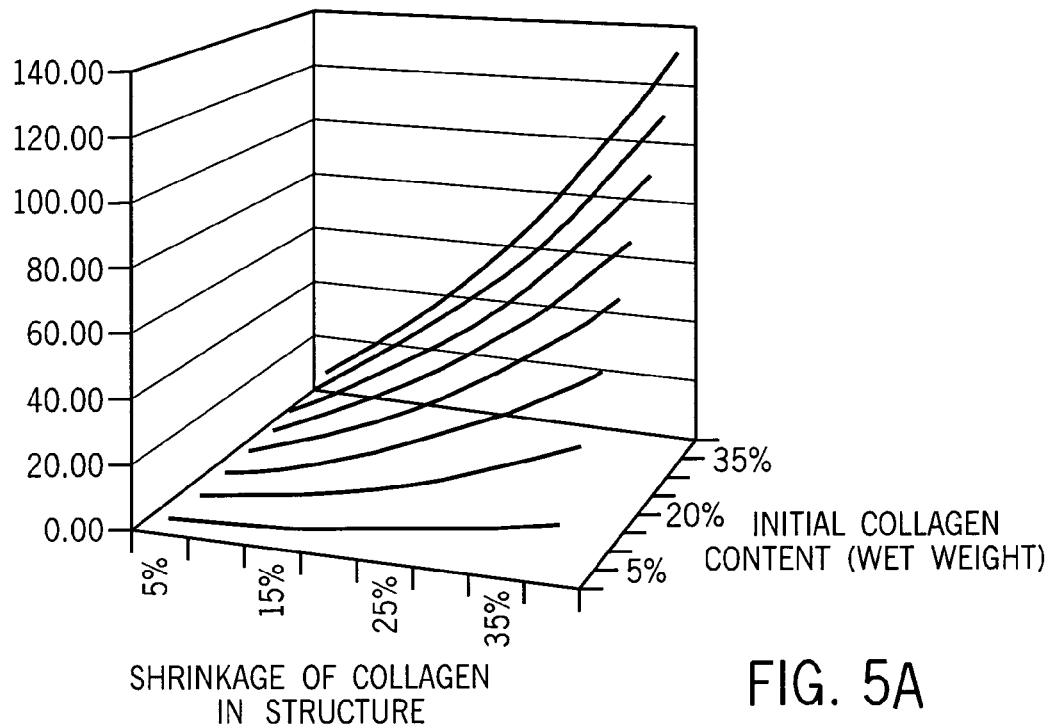
FIG. 5A shows changes in acoustic velocity as a function of initial collagen content and percentage of collagen shrinkage.
Figure 5B:
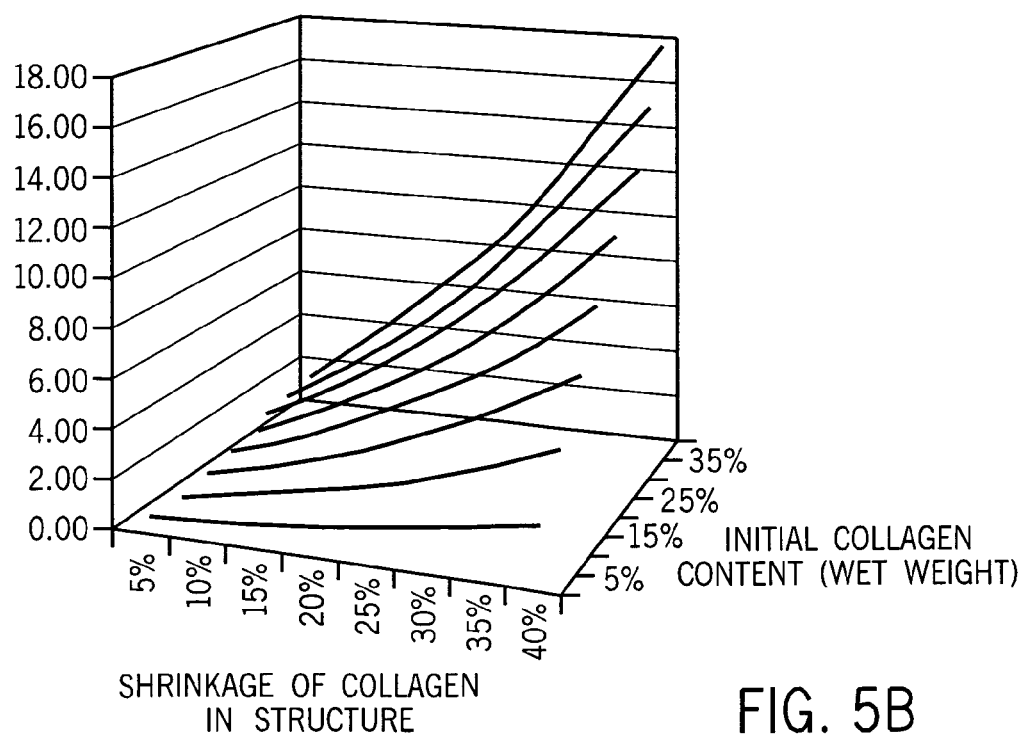
FIG. 5B shows changes in acoustic attenuation as a function of initial collagen content and percentage of collagen shrinkage.
Figure 6:
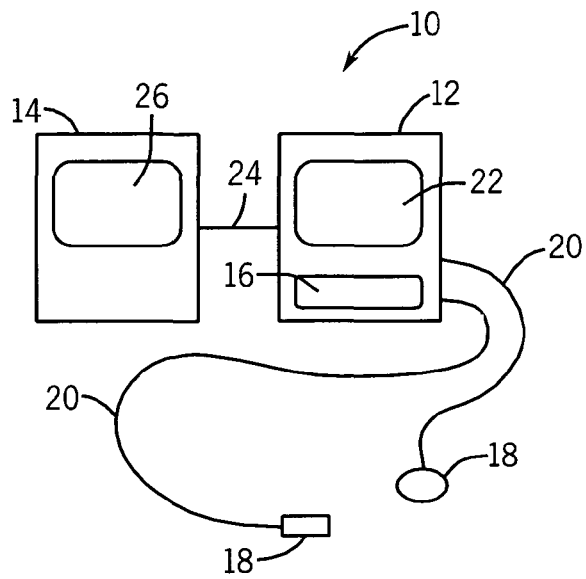
FIG. 6 shows a system for monitoring and mapping of tissue collagen shrinkage using ultrasound backscatter information and/or measured acoustic data reflected from or transmitted through tissue structures.

An example of a system 10 which can be used to implement the principles of the present invention is shown in FIG. 6. The system 10 includes an ultrasound imaging device 12 to which a tissue change mapping workstation or system 14 is connected. The ultrasound imaging system 12 includes a computer/microprocessor 16 and a transmitter/transducer/receiver unit 18. The transmitter/transducer/receiver unit 18 is coupled to the computer 16 through an electrical cable 20. The transmitter/transducer/receiver unit 18 emits ultrasound energy and receives the energy backscattered by the tissue. This information is provided to the computer 16 which processes the backscattered data to generate images displayed on a display screen 22. Such ultrasound imaging systems are well known within the art. The tissue mapping workstation 14 is shown coupled to the computer 16 for communication of image data through an electrical cable 24 or other conventional method (wireless, e.g.).

The system 10 of the present invention can be used in conjunction with any conventional thermal treatment device such as a microwave, laser, RF, electrocautery, or ultrasound therapeutic device; but the use of the system 10 is not limited to such applications. For example, the system 10 can be used to monitor changes in collagen or tissue structure which is responding to a chemical, either injected into the tissue or administered topically.

The display of image data on the screen 22 of the ultrasound imaging device 12 is well known and can be represented in several forms. In operation of the system 10, ultrasound energy is emitted from the transmitted portion of transmitter/transducer unit 18 towards the tissue to be displayed. This energy is backscattered differently by different types of tissue. This backscattered ultrasound energy is comprised of spectral reflection and interference reflection portions. The backscattered energy is received by the transducers of the transmitter/transducer 18 and converted to grayscale intensity data. The grayscale intensity data is stored in shared memory, a video RAM or similarly disposed within the system 10. The grayscale intensity data is retrieved from an integral and conventional memory or video RAM and used to generate the driving signal for the display screen 22. In another embodiment of the invention, the ultrasound signal is transmitted through the tissue and received by a transducer on the opposing side. This through transmission signal is then converted to grayscale intensity data and displayed on the display screen 22. Most commercially available ultrasound systems provide a video data port so the signal used to drive the display 22 may be recorded. This port is typically a RS-170 port and the data provided through such ports are well known. Alternatively, there are ultrasound imaging systems that provide for digitally interfacing with an external form of the computer 16; and both the data are received from the ultrasound imaging system in digital form and processed and displayed on the system 10. Such ultrasound systems 10 often also provide for digital control of a number of the ultrasound system operating parameters, such as field of view, video settings, image probe selection, internal ultrasound imaging system processing settings, and similar functions. A few ultrasound imaging systems 10 also provide access to the raw RF data prior to any internal processing within the ultrasound imaging system.

Preferably, the mapping workstation 14 either receives the video data signal from the video data port and digitizes the signal to generate pixel data or interfaces to an available digital interface port on the ultrasound imaging system 10. Since most conventional ultrasound systems have a RS-170 port or other video output connector, such an implementation makes the workstation 14 compatible with most available ultrasound systems. Alternatively, the workstation 14 can couple to the system 10 through a parallel, serial, USB, or IEEE1394 data port to communicate pixel or grayscale data with the system 10, as well as control the ultrasound imaging. An example is the Terason system with an IEEE-1394 interface. This structure has the advantage of providing grayscale data from the system 10 prior to the data undergoing signal processing in the system 10. The system 10 may perform signal processing which reduces sensitivity to the information available in the interference reflection component of the backscattered energy. This reduction in sensitivity may affect the accuracy of the detection of collagen or other tissue structural changes by the workstation 14. By obtaining pixel data prior to the ultrasound imaging system 10 processing it, the information in either of the reflection or transmission components may contribute to more accurate tissue mapping. Additionally, pixel data generated by the system 10 may contain textual information that may complicate its processing for the tissue change mapping. The transfer of either analog or digital image data or their equivalents for tissue change or collagen mapping is within the scope of the principles of the present invention.

Grayscale data is a data word which defines an intensity level for a pixel of a display. The lowest value of the grayscale range corresponds to a low intensity or black shade pixel while the high value of the range corresponds to the brightest intensity or white shade pixel. The intervening values are a shade of gray, hence the term grayscale data. Grayscale data may be displayed on a screen capable of displaying color data. The display 22 of ultrasound system 10 and the display 26 of the workstation 14 are displays capable of displaying both grayscale and color images.

Preferably, the mapping workstation 14 for monitoring tissue structural changes and/or collagen changes includes a personal computer or the like with an Intel Pentium Duo or AMD processor or equivalent or better processor, 533 MHz or faster FSB, 512 MB or more of RAM and a 40 GB or larger hard drive. Digital signal processing can be performed on workstation 14 or by a separate digital signal processing card coupled to the system 10 through its system bus which processes the image data from system 10 to perform the mapping of changes to tissue structure or collagen. The image data to be processed may be displayed on the display 26 of the system 10. Additionally, the system 10 can include standard input/output (I/O) devices such as a mouse or trackball for moving a cursor about the image displayed or the display 26 and for identifying coordinates on the image.

Figure 7:
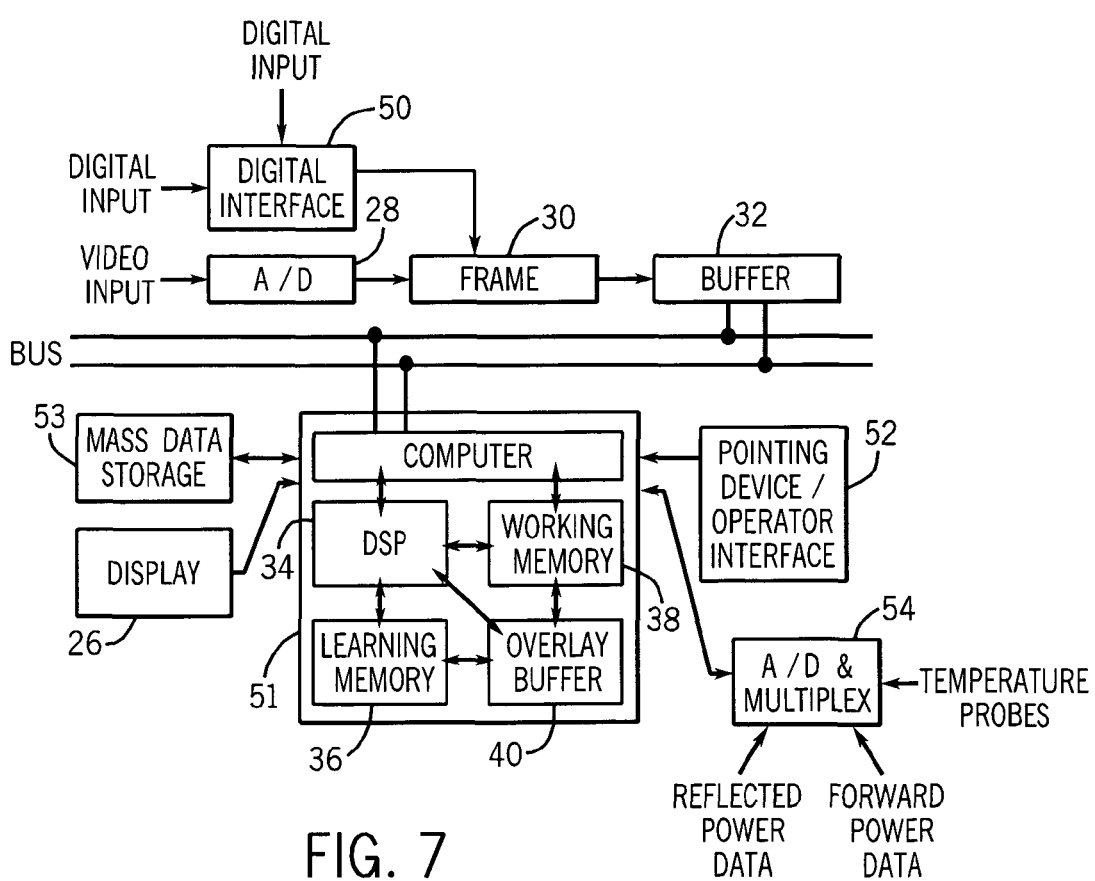
FIG. 7 shows a block diagram of one form of the tissue mapping workstation.

FIG. 7 is a block diagram of a digital signal processing approach within the workstation 14 used to implement the tissue mapping of the present invention. The system 10 includes a frame grabber 30, a data buffer 32, a computer 51 including data signal processor 34 for executing appropriate conventional computer software, a learning set memory 36, a working memory 38, and an overlay buffer 40. The frame grabber 30 retrieves video data from a video data port one frame at a time and converts the analog video data to pixel data which is stored in the data buffer 32 for processing. Alternatively, the frame grabber 30 can receive data from a digital interface 50 which communicates with the system 10 through a digital data port to obtain grayscale data generated by the system 10. The grayscale data is used by the system 10 to produce the video signal which drives display 22 and may or may not undergo digital signal processing prior to its transfer to the workstation 14. Typically, frame data is provided to the display 22 at a rate of approximately 9 to 30 frames a second. To attenuate noise in the image data, several frames of data may be retrieved and averaged for each pixel. This averaged pixel data may then be stored in the data buffer 32 for processing by the processor 34 within the workstation computer 51.

Prior to initiation of thermal treatment, a treating physician preferably selects a region of interest within the image displayed on the display 26, although the entire display 26 may be identified as the region of interest. The region may be identified by using a pointing device 52 to outline the region of interest. The system 10 evaluates the image data within the region of interest during the monitoring period for mapping of tissue changes. Preferably, the region of interest is defined by clicking on a first and second location on the display 26 to define an upper left and lower right corner of a rectangle or square, although other region shapes may be used. Once the region of interest is defined, the data signal processor 34 segregates the region of interest into predefined groups of pixels for temperature mapping. A group of pixels may be defined as a single pixel. Preferably, the groups of pixels contain multiple pixels. Multiple pixel groups are less sensitive to ultrasound probe position changes. Preferably, the groups of pixels segregate the region of interest into an integer number of pixel groups.

Once the region of interest and groups of pixels are defined, the data signal processor 34 and/or the computer 51 preferably generates a neural element for each group of pixels and builds a learning set of initial baseline values and transfer functions for each neural element. The baseline values are stored in the learning set memory 36. Baseline values for a group of pixels are discussed in more detail below. The baseline values provide information to the data signal processor 34 about the homogeneity of a group of pixels and its surrounding neighborhood. This baseline information may be used to detect changes caused by thermal treatment which are correlated to temperature values and changes.

One set of baseline values for a group of pixels may include a differential measurement of the grayscale values within and outside a group of pixels. For example, an average grayscale value for a group of pixels may be computed and differential grayscale value for each pixel bordering the pixel group may be calculated and accumulated. Such a measurement provides an indication of the smoothness of the image in the area of the pixel groups. Likewise, gradients related to grayscale values at the boundaries of a pixel group may be used to define the change in an image area prior to initiation of thermal treatment. Other examples of baseline values include the detection, counting, and measurement of edges in the vicinity of a pixel group. Such edge detection and measurement may be performed using threshold, gradient, and Canny techniques, which are well known in the art. These techniques provide a baseline measurement for detecting and counting of edges in the vicinity of a pixel group, the smoothness of the image in the area of the pixel group, the homogeneity of the area around the pixel group, the similarity of the areas on opposing sides of the pixel group, a measure of the amount of grayscale change in the area of the pixel group, respectively. By using these techniques to establish baseline values and then compute changes in these values as tissue structural change occurs, differential values indicative of the amount of change caused by the treatment-induced structural changes may be discerned and quantized.

After thermal treatment begins, the data signal processor 34 uses the pixel values stored in the buffer 32 for new image frame data to generate new transfer function elements of the image currently being displayed. These compared to the learning data in the learning set memory 36 to measure an image change for each group of pixels within the region of interest. The measured image change, typically expressed in grayscale units, is correlated to changes in collagen and/or tissue structure for the tissue area corresponding to the pixel group. This change is compared to thresholds for the structural/collagen physiological change ranges to ascertain the particular range in which the tissue resides. Identification of a specific structural/collagen/thermal dose range for a pixel group is then used to generate overlay image data which is stored in the overlay buffer 40. The overlay image data is converted to analog frame data and provided to the display 26. The overlay image data is displayed on portions of the image on the display 26 as a colorwash overlay to indicate degree of collagen/structural change for tissue areas corresponding to the groups of pixels. Alternatively, the overlay image data may remain in digital form and an I/O controller implemented for communicating the pixel data to the system 10. The pixel data may be stored in the video RAM of the system 10 and used to colorwash overlay a portion of the display 22 to indicate degrees of tissue structural changes for each group of pixels within a region of interest.

Figure 8A:
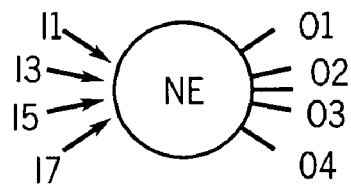
FIG. 8A shows a diagram of a neural element with four inputs for determining changes in backscatter associated with a structural change in a small tissue region to determine the magnitude of change for a pixel or group of pixels.

An example neural element ("NE") is shown in FIG. 8A. The neural element NE implements a transfer function which correlates the input data I to an output condition O. If an actual reading of the output condition is possible, the difference between the correlated output condition O and the actual condition is used to modify the transfer function so it better correlates the input data I to a corresponding output condition O. In this way, the element NE adjusts or learns during an ongoing process. In the present invention, this adjustment in the neural elements permits the system to compensate for changes in the tissue caused by local physiological changes unassociated with changes in structural elements. In this example, the neural element receives four inputs, I1, I3, I5 and I7. These inputs describe the neural element and the neural element corresponds to a pixel or group of pixels identified by the process discussed above. The transfer function in element NE of FIG. 8A correlates the difference between a weighted average of the current transfer function and a baseline condition for the transfer function contained in the learning set to a collagen change for the pixels corresponding to the element NE. This tissue collagen change results in activation of one of the four outputs. The outputs indicate whether there is no change (O1), the change is reversible (O2), the change is greater than 50% irreversible (O3), or the change is caused by irreversible ablation (O4). Preferably, these ranges correspond to the ones expressed in terms of percentage change in collagen structure. The use of four descriptors for a neural element is merely exemplary and more or fewer descriptors may be used for each element covering different ranges.

Figure 8B:
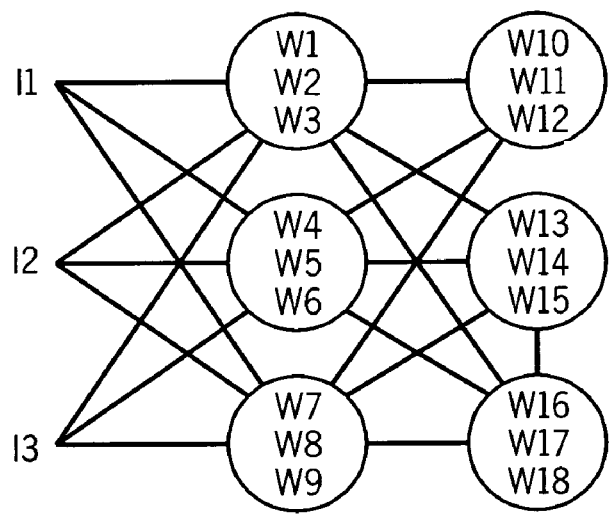
FIG. 8B shows a preferred neural network with three inputs for each group of pixels.

A preferred neural network for each group of pixels is shown in FIG. 8B. That network shows three inputs for a set of three transfer functions, although fewer or more may be used for a group. The vector path transfer functions are measurements between a group of pixels and its neighbor groups. These inputs are each provided to four neural elements which weight them differently to compute a weighted average. These weighted averages are each applied to the output elements, one of each corresponds to a temperature range. The output elements weight the applied averages and one of the output elements is activated. Preferably, the output elements are also provided with a thermal dose correlation factor to verify whether the correct output element was activated. If there are any errors, an adjustment signal is generated and supplied to the neural elements providing the erroneous weighted average to adjust the weighting factors W at the neural element. The states of the output elements for each group of pixels are used to generate the overlay colorwash image data.

Figure 9A:
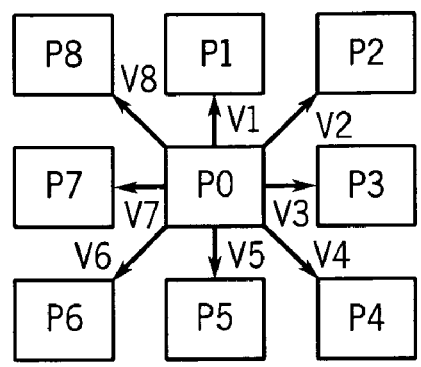
FIG. 9A shows a diagram of the surrounding pixels used to define a set of vectors used to determine the transfer function for a single pixel.
Figure 9B:
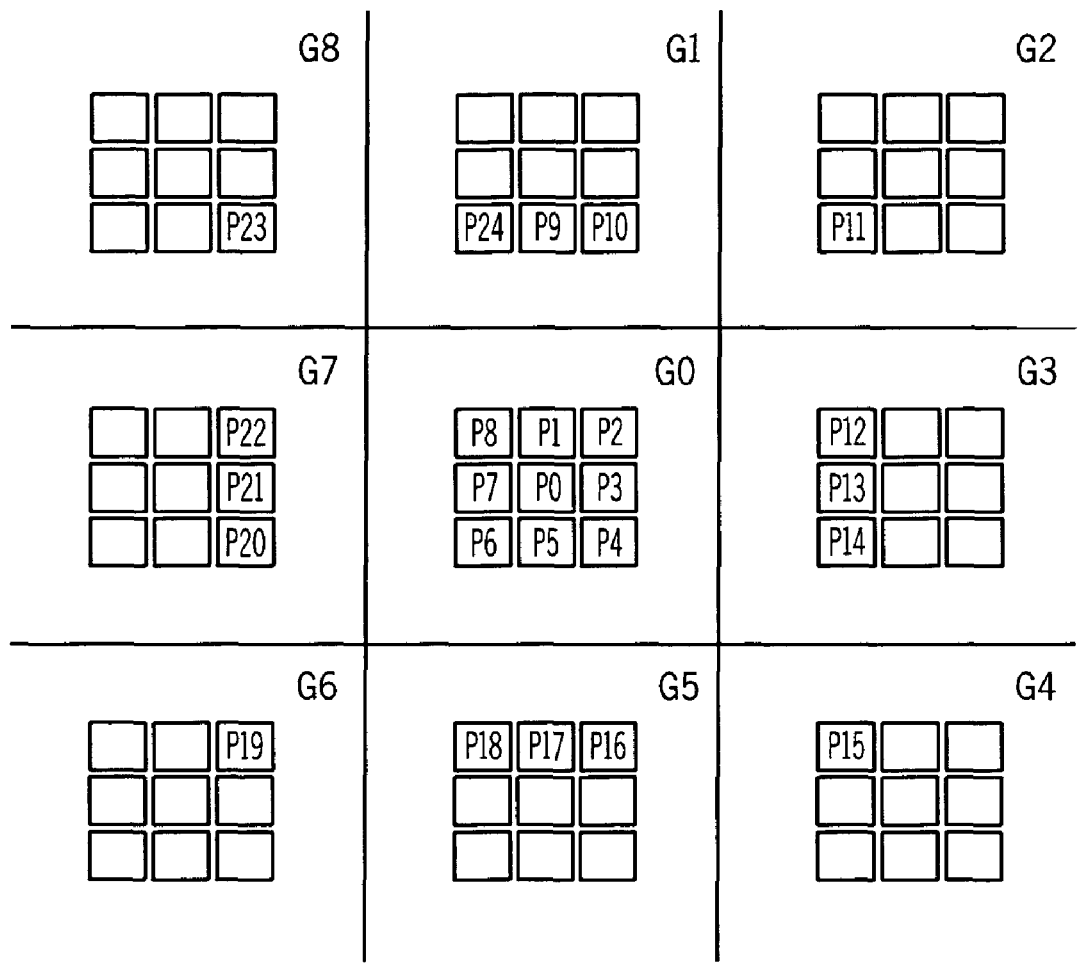
FIG. 9B shows a diagram of groups of pixels used to define the vectors for a transfer function for a region of interest group made up of multiple pixels.

The pixels which can be used to generate a transfer function are shown in FIG. 9A. The center pixel P0 is the pixel for which a change is to be determined. The immediately adjacent pixels P1-P8 are used to define input data I1-I8. These input values are defined by the difference between P0 and one of the adjacent pixels. For example, I1 is defined by the difference in the detected grayscale between P0 and P1, I2 the difference between P0 and P2, and so on. For groups of pixels, adjacent groups may also be utilized in the edge detection and measurements. In FIG. 9B, pixels P9-P24 are adjacent to the region of interest. A weighted average of all or some of these weighted inputs may be used to define an input function for P0. In a similar manner, this may be defined for a group of pixels. As shown in FIG. 9B, the group of pixels denoted by GR0 are surrounded by pixel groups GR1-GR8. In such a case, the transfer function may be defined by the average of the difference between each of the pixels in the top row of GR0 and the adjacent pixels in GR1. Other transfer functions may be similarly defined for other adjacent regions.

The input function for a group of pixels may be derived from four or more vectors about a pixel group. The vectors, V1-V8 for a single pixel, are shown in FIG. 9A. In FIG. 9B, the vectors may correspond to the eight surrounding groups about the center region GR0 or they may be defined as the single row, column and diagonal vectors extending from the center pixel of GR0. The important aspect of selecting a set of vectors is to define neighboring pixels in groups which provide information about the area about a pixel group so changes may be detected as they approach a pixel group or as they emanate from a pixel group.

Figure 10:
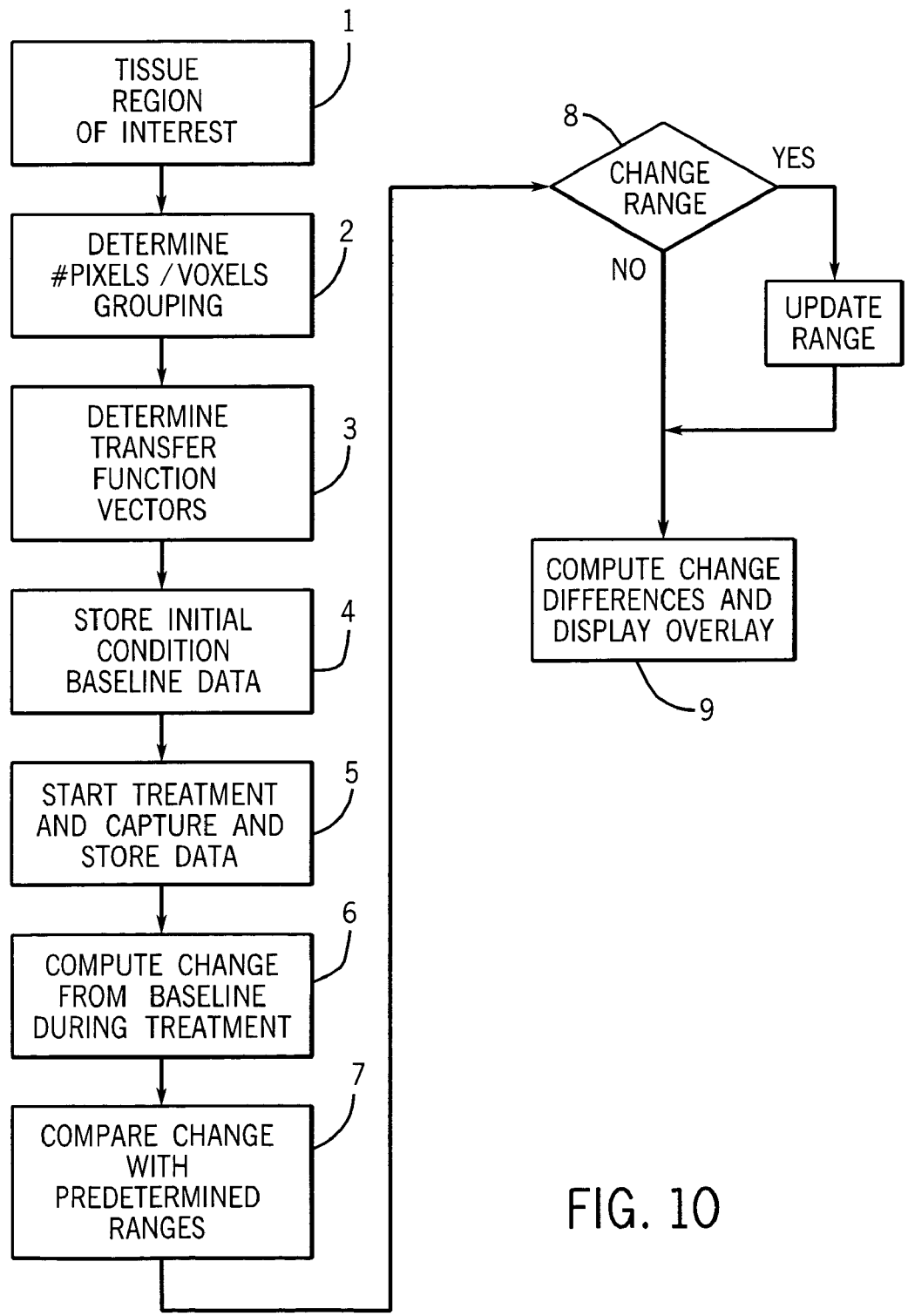
FIG. 10 shows a flow diagram of a method for monitoring and displaying on a workstation the changes in collagen/tissue structure during a therapy procedure.

The method of the present invention may be expressed in a flow chart as shown in FIG. 10. The treating physician preferably begins by selecting the region of interest (Step 1). The gain of the ultrasound system is adjusted until the number of pixels at the lower intensity levels dominate the region of interest. In that way, the displayed image is predominated by intensity levels which permit the pixels to change to the higher end of the grayscale which in turn makes a greater dynamic range of tissue structural change mapping possible.

The region of interest is then segregated into groups of pixels (Step 2). After groups of pixels are defined, a set of vectors is selected for each pixel group and a transfer function which best maps the selected set of vectors to the detected normal homeostasis is selected (Step 3). The vectors may be differential edge detection or gradients. Baseline values are determined and placed in the learning memory associated with the neural element (Step 4). The mapping workstation 14 is then ready and tissue treatment may begin. This indication may be generated by displaying a message on the display 26, or by some other indicator.

During treatment, image data from the system 10 is captured and stored in the buffer 32. The vectors for each neural element are updated and input to the neural elements (Step 5). The neural elements compute a current transfer value and measure the differential between the current element value and the baseline or initial value (Step 6). The current value is stored in the memory. Preferably, the thermal dose for the tissue in which a temperature probe is implanted is determined and the differential change in thermal dose is measured. This change is correlated to the change in tissue/collagen structure and to the change in grayscale value between the initial set of transfer function descriptors for the corresponding neural element and the current value (Step 7). If this grayscale unit to thermal dose correlation factor is approximately the same as the one being used by the neural elements, the process continues. Otherwise, the correlation or weighting factors for the transfer functions of the neural elements are modified.

Using the thermal dose correlation factor, each neural element computes a structural change corresponding to the grayscale differential between the initial value and the current value (Step 8). The differential is added to the measured initial value to determine the degree of change for the tissue. If this change is greater than one of the threshold doses for the thermal treatment ranges (Step 9), the information corresponding to the detected structural change is generated, stored in the overlay image buffer 40, and displayed as an overlay onto the image on the display 26. The overlay data is colorized or colorwashed to display a change indicative of the amount of thermally-induced structural change for a feature corresponding to a group of pixels.

The system 10 described can also use one or more temperature probes to confirm the grayscale-to-collagen change correlation factor. In an alternative embodiment, no temperature probes are used. Instead, the physician directs the treating device at a tissue region being imaged and delivers a short burst of treating radiation. The power of this radiation and its duration is provided to the mapping system which uses this information with a tissue energy absorption factor to calculate a power deposition for the tissue. The power deposition corresponds to a known thermal dose for the type of tissue identified for the feature. This change from baseline is correlated to the grayscale differential measured for the same region during the test pulse. This is done two or three times to confirm or calculate an average correlation factor for the region. A corresponding correlation factor for other tissue types may be extrapolated from that data using known methods. Yet another alternative embodiment to determine the correlation factor is to match multiple levels of histologically determined tissue changes with the changes in backscatter affecting the transfer function of the neural elements. Once the correlation factor is calibrated in this manner, use of the system proceeds as described above except the steps related to using the temperature measured by the probe to adjust the system are not performed. Yet another alternative embodiment would utilize unprocessed front-end data from the ultrasound system 10 by monitoring either the reflected signal or the transmitted signal through the target tissue. Measured changes in the reflected and/or transmitted signal would then be correlated with multiple levels of histologically determined tissue changes and/or with different levels of delivered thermal dose.

Additionally, the expert part of the system 10 of the present invention can verify that the grayscale differential is therapeutically induced and not caused by signal noise, thus applying pattern recognition. To verify the differential, the expert system can use edge detection techniques on the histogram data stored for a neural element to determine whether the gradient established by prior transfer function values confirms the shift in histological/structural/dose range. Additionally, differences between a current transfer function value for one neural element and the current value for its neighboring neural elements can also be evaluated using edge detection or imaging enhancement techniques to confirm whether the area in the vicinity of the neural element is approaching or at an greater level of structural change. Additionally, or alternatively, the histogram data can be processed using filtering or other noise alternating techniques to determine whether the current descriptor set accurately defines a tissue or image change. Thus, the histogram image data for each neural element and the descriptor set values for neighboring neural elements can be used to confirm the collagen/structural change for a region.

In use, the treating clinician prepares a patient for thermal treatment of a targeted tissue area. After the mapping workstation or the mapping system 14 has established baseline values for the transfer function for each neural element, the mapping system 14 signals the clinician that treatment may begin. The treating clinician then inserts or applies the treating probe/device to a patient by a selected method and directs the emitted energy towards the target area. As the emitted energy is absorbed in the target area, the mapping system 14 periodically captures pixel data. The captured data is used to update the transfer function values which are compared to the baseline values to generate a grayscale differential. The update rate depends upon the digital signal processor used and the speed and amount of memory. In a preferred embodiment, the Integral Technologies video capture card updates video data at a rate of 15-30 frames/second. The grayscale differential is correlated to a tissue collagen/structural change by using a grayscale-to-temperature correlation factor. The corresponding change determined for the tissue corresponding to the neural element is compared to the measurement change threshold for the treatment ranges. In an alternative embodiment of the invention, unprocessed front-end data from the ultrasound system 10 is monitored from either the reflected signal or the transmitted signal through the target tissue. Measured changes in the reflected and/or transmitted signal would then be correlated with multiple levels of histologically determined tissue changes and/or with different levels of delivered thermal dose and this result mapped onto the display over the number of pixels interrogated. If the differential for a pixel value indicates that the structural state of the tissue has shifted to another zone, the mapping system 14 can confirm the change degree zone shift by using edge detection techniques on the histogram data for the neural element or by using edge detection techniques on the vector set values for the neural elements adjacent to the neural element under investigation. Preferably, the mapping system 14 reads one or more temperature probes implanted in the tissue to confirm the grayscale-to-thermal dose correlation factor used by the neural elements. When a range shift is detected for the tissue corresponding to a neural element, the mapping system 14 stores color overlay data in the overlay buffer 40 which is transmitted to the video RAM 22 to modify the display 26. As the treating physician observes the addition of color to the displayed image, the probe may be relocated or the energy being supplied to the target area adjusted. Once the treating physician is satisfied that the target area tissue has been appropriately treated, the treatment may cease and the treating probe removed. If the treating physician desires to continue monitoring of the area, the transmitter/transducer unit 18 is used to continue the generation of image data which is compared to the baseline by the expert system to indicate degree of collagen/structural change in the tissue. In another embodiment of the invention, the system may establish a predetermined limit for tissue modifications and automatically cease treatment when the stipulated limit is achieved.

While the present invention has been illustrated by a description of preferred and alternative embodiments and processes, and while the preferred and alternative embodiments and processes have been described in considerable detail, it is not the intention of the applicants to restrict or in any way limit the scope of the appended claims to such detail. Additional advantages and modifications will readily appear to those skilled in the art. For example, the change in the backscattered data may be detected in the signals received by the transmitter/transducer unit 18. As a result, the signals generated by the transducers in the unit 18 may be processed by a system built in accordance with the principles of the present invention to determine changes in collagen or tissue structure. Such a system is within the scope of the present invention. Likewise while the invention has been described with reference to images generated by ultrasound energy, the system and method of the present invention may also be used with image data generated from other electromagnetic imaging/detection modalities, such as microwave reflection/transmission detection systems, radiographic imaging methods, and other methods for tomographic transmission measurements of ultrasound, light, microwaves, radiographic, or other imaging energy sources. An example of an electromagnetic system would be an array of small microwave apertures placed adjacent to the target tissues on one or both sides of the body region containing the target tissues. The antenna device apertures can be simultaneously or independently excited in either a continuous mode or a pulsed mode. Either or both the reflected and transmitted signals may be monitored and processed in a manner described in this invention description. Similarly, tomographic radiographic data taken either continuously or at intervals during a treatment may be processed with this invention to yield tissue structural change information during therapy. These are examples only and other imaging methods may be similarly used and processed.

What is claimed is:

1. A system for measuring collagen structural changes responsive to collagen treatment, comprising:
   an imaging unit for sending into and receiving acoustic signals from collagen containing tissue of interest;
   a computer based data analysis system having stored data relating ultrasound tissue thermal dose to histological changes in collagen structure for correlating a thermal dose applied to the tissue of interest to a change in collagen in the tissue undergoing structural changes arising from the collagen treatment computer software stored in the computer based system configured to process and output the received acoustic signal to the data analysis system to generate an acoustic grayscale differential signal to provide a correlation function which is thereby descriptive of structure of the collagen in the tissue, the system not requiring or including a temperature probe, for the collagen being treated;

the imaging unit and data analysis system for processing via the computer software to further provide a grayscale differential signal characteristic of a baseline image area from the collagen containing tissue before being treated, the system thereby configured to define changes in the image area over that present prior to initiation of the collagen treatment; and the data analysis system and imaging unit further configured to use the changes in the acoustic grayscale differential signal from the collagen containing tissue to provide a qualitative metric of collagen shrinkage in the collagen containing tissue, thereby being able to determine the effect of the collagen treatment on the collagen containing tissue.

2. The system as defined in claim 1 wherein the data analysis system includes computer software executed by the computer based data analysis system to assign color values from the changes of the grayscale differential signal to at least one pixel of the imaging unit corresponding to differing changes in the collagen shrinkage in the collagen containing tissue represented by at least one pixel of the imaging unit.

3. The system as defined in claim 1 further including a collagen treatment device wherein the collagen treatment device comprises at least one of a microwave unit, a laser unit, an RF unit, an electrocautery unit, a thermal unit, and an ultrasound unit.

4. The system as defined in claim 1 wherein the data analysis system assigns color values to imaged pixels of the imaging unit corresponding to differing changes in the collagen containing tissue properties in the tissue region represented by the pixels; and generating an overlay data to display said color-coded pixels over a standard acoustic image.

5. The system of claim 1, wherein the at least one image element is a pixel.

6. The system as defined in claim 1 further including computer software which includes a computer program to notify a user of the system when collagen shrinkage has reached a predetermined amount of shrinkage.

7. The system as defined in claim 6 wherein the computer program analyzes changes in acoustic velocity characteristic of changes in collagen structure to determine the collagen shrinkage.

8. The system as defined in claim 6 wherein the computer program analyzes changes in acoustic attenuation characteristic of changes in collagen structure to determine the collagen shrinkage.

9. The system as defined in claim 6 wherein the predetermined amount is about 20%.

10. The system as defined in claim 1 wherein real time changes in acoustic signal from the collagen containing tissue are selected from the group of changes in acoustic velocity and changes in acoustic attenuation.

11. The system as defined in claim 1 wherein the acoustic grayscale differential signal consists of an unprocessed RF signal.

12. The method as defined in claim 1 wherein the acoustic grayscale differential signal is selected from the group of a backscattered signal and a transmitted signal.

13. A system for measuring collagen structural changes responsive to collagen treatment, comprising:

an imaging unit for sending into and receiving acoustic signals from collagen containing tissue of interest;

a computer based data analysis system having a stored computer program for constructing neural elements descriptive of a transfer function for characterizing changes in collagen from the treatment and the system further having stored data relating ultrasound tissue thermal dose to histological changes in collagen structure for correlating the computer generated neural elements of the transfer function, characteristic of tissue thermal dose, to actual changes in the collagen containing tissue undergoing structural changes at a tissue region arising from the collagen treatment based upon a measured change of an acoustic grayscale backscatter image which establishes the transfer function;

the imaging unit and computer based data analysis system processing acoustic signals received from the tissue after treatment to provide neural elements of the transfer function to provide a correlation function, without use of a temperature probe of tissue temperature, for the collagen being treated, the correlation function descriptive of the changed collagen structure using data from the acoustic grayscale image generated and further processing a grayscale differential image from the collagen containing tissue characteristic of a baseline image area before being treated, the system thereby being configured to define changes in the image area over that present prior to initiation of the collagen treatment to provide a corrected correlation function; and the data analysis system further configured to use the corrected correlation function and further configured to provide a qualitative metric of collagen shrinkage in the collagen containing tissue, thereby being able to determine the effect of the collagen treatment on the collagen containing tissue.

14. A system for measuring collagen structural changes responsive to collagen treatment, comprising:

an imaging unit for sending into and receiving acoustic signals from collagen containing tissue of interest; and a computer based data analysis system including a stored computer program and having stored data relating ultrasound tissue thermal dose to previously measured histological changes in collagen structure and further processing data arising from the collagen treatment based upon a measured change of the acoustic unprocessed front end RF data of transmitted or reflected ultrasound signal from the collagen containing tissue signal being treated and comparing to the stored data to provide a correlation function by executing the computer program to process the front end RF data and stored data, without use of a temperature probe for direct measure of tissue temperature for the collagen containing tissue, to provide data descriptive of changed collagen structure relative to the stored data; and the data analysis system further configured using the computer program to analyze changes in the unprocessed front end RF data of transmitted or reflected ultrasound signal from the collagen containing tissue to provide a qualitative metric of collagen shrinkage in the collagen containing tissue, thereby being able to determine the effect of the collagen treatment on the collagen containing tissue.

15. The system as defined in claim 14 wherein the computer program analyzes changes in RF data characteristic of changes in collagen structure to determine the achieving a threshold for completed collagen shrinkage.

16. A system for measuring collagen structural changes responsive to collagen treatment, comprising:
- an imaging unit for sending into and receiving acoustic signals from collagen containing tissue of interest;
- a computer based data analysis system and stored computer program, the system having stored data relating ultrasound tissue thermal dose to known histological changes in collagen structure, the computer software executing a program for correlating a clinical tissue thermal dose applied to the collagen containing tissue to the stored data to determine a change in collagen containing tissue undergoing structural changes at a region arising from the collagen treatment based upon a measured change by the imaging unit of an unprocessed RF data signal for both the tissue and the stored data to provide a correlation function which is thereby descriptive of collagen structure which has been treated, without use of a temperature probe for direct measure of tissue temperature, for the region generated for at least one image element representative of the region having the clinical tissue thermal dose within the collagen containing tissue and further compared to a measured RF signal from a test pulse from the region for removing background signal; and
- the data analysis system and imaging unit further configured to use changes in the RF data signal from the collagen containing tissue compared to the stored data and to provide a qualitative metric of collagen shrinkage in the collagen containing tissue, thereby being able to determine the effect of the collagen treatment on the collagen containing tissue.

17. The system as defined in claim 14 wherein the data descriptive of the changed collagen structure is further compared by the computer program to the front end RF data signal from a baseline image area of the collagen containing tissue before treatment for removing a background signal from data accumulated during the collagen treatment; and
- the data analysis system further configured using the computer program to analyze changes in the unprocessed front end RF data of transmitted or reflected ultrasound signal from the collagen containing tissue corrected for the background signal, for the collagen containing tissue region and the data analysis system configured to provide a qualitative metric of collagen shrinkage in the collagen containing tissue, thereby being able to determine the effect of the collagen treatment on the collagen containing tissue.

* * * * *